United States Patent
Sakuth et al.

(10) Patent No.: US 6,552,236 B2
(45) Date of Patent: Apr. 22, 2003

(54) PROCESS FOR THE CLEAVAGE OF ALKYL TERT-ALKYL ETHERS INTO ISOOLEFINS AND ALKANOLS OVER ACID CATALYSTS

(75) Inventors: Michael Sakuth, Marl (DE); Axel Tuchlenski, Recklinghausen (DE); Dieter Reusch, Marl (DE); Andreas Beckman, Recklinghausen (DE)

(73) Assignee: OXENO Olefinchemie GmbH, Marl (DE)

( * ) Notice: Subject to any disclaimer, the term of this patent is extended or adjusted under 35 U.S.C. 154(b) by 55 days.

(21) Appl. No.: 09/841,043

(22) Filed: Apr. 25, 2001

(65) Prior Publication Data

US 2002/0010379 A1 Jan. 24, 2002

(30) Foreign Application Priority Data

Apr. 28, 2000 (DE) .......................... 100 20 943

(51) Int. Cl.⁷ .......................... C07C 27/00; C07C 27/18; C07C 29/00; C07C 29/10; C07C 1/00
(52) U.S. Cl. ...................... 568/907; 585/639
(58) Field of Search ................ 568/907, 886, 568/888, 889, 890; 585/639, 636

(56) References Cited

U.S. PATENT DOCUMENTS 4,287,379 A * 9/1981 Brunner et al. ............. 585/839
5,518,699 A * 5/1996 Kashnitz et al. ............ 422/211
5,849,971 A    12/1998 Sakuth et al.

FOREIGN PATENT DOCUMENTS

| DE | 35 09 292 | 12/1985 |
| DE | 36 10 704 | 10/1987 |
| DE | 43 22 712 | 1/1995 |
| EP | 0 302 336 | 2/1989 |
| EP | 0 726 241 | 8/1996 |

OTHER PUBLICATIONS

B. Schleppinghoff, et al., Jahrgang, vol. 104, No. 4, pp. 173–177, "Hochreine Isoolefine Durch Reaktionen and Speziellen Ionenaustauschern," (Ultrapure Olefins 1–16 Via Reaction on Specific Ion Exchange Resins), Apr. 1998.
Derwent Abstracts, AN 1998–099500, RU 2083541, Jul. 10, 1997.

* cited by examiner

*Primary Examiner*—Samuel Barts
*Assistant Examiner*—Elvis O. Price
(74) *Attorney, Agent, or Firm*—Oblon, Spivak, McClelland, Maier & Neustadt, P.C.

(57) ABSTRACT

Alkyl tert-alkyl ethers are cleaved into the corresponding isoolefins and alkanols by a process comprising acid-catalyzed reactive distilling an alkyl tert-alkyl ether fed into the reaction zone of a reactive distillation apparatus as an azeotrope of the alkyl tert-alkyl ether and the corresponding alkanol, wherein the reactive distillation apparatus is configured from bottom to top as a bottom zone, at least one distillation zone and a reaction zone. The process is suitable for the cleavage of primary, secondary and tertiary alkyl tert-alkyl ethers, in particular MTBE.

18 Claims, 1 Drawing Sheet

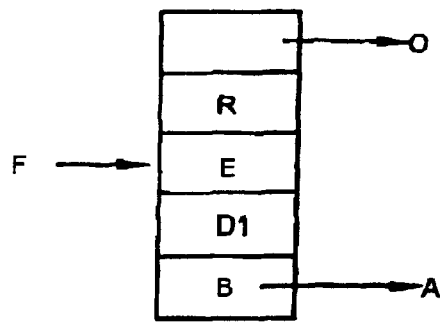
(Fig. 1)
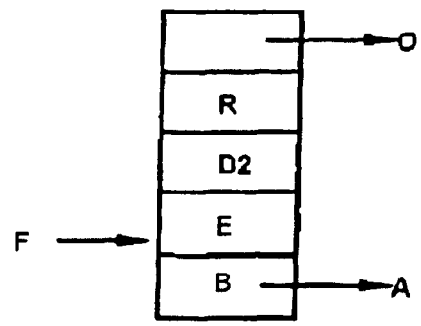
(Fig. 2)
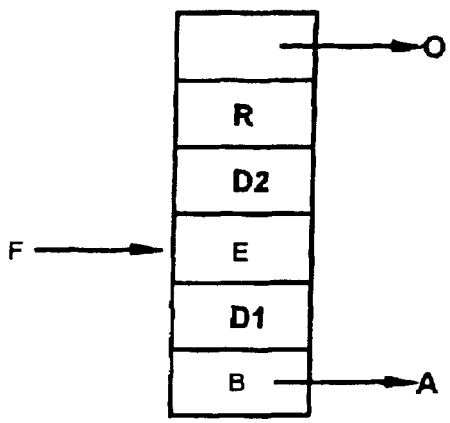
(Fig. 3)
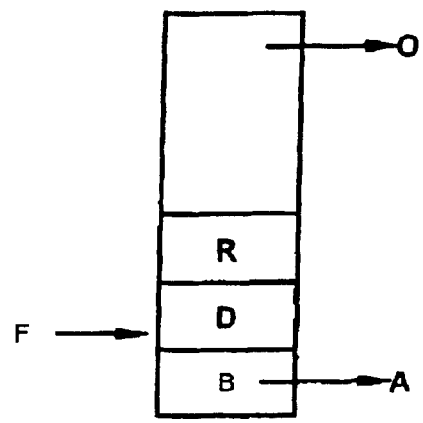
(Fig. 4)
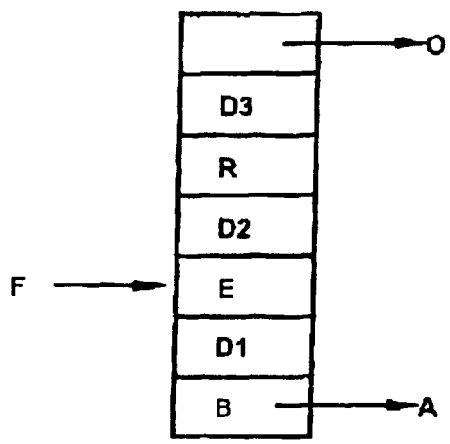
(Fig. 5)
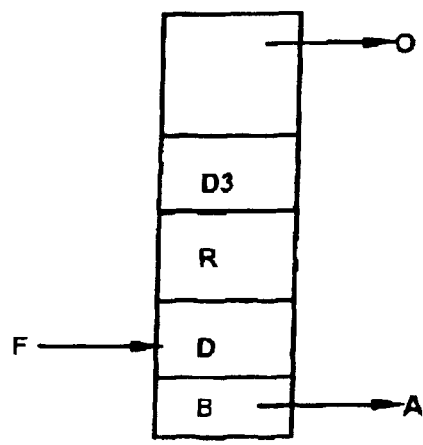
(Fig. 6)

PROCESS FOR THE CLEAVAGE OF ALKYL TERT-ALKYL ETHERS INTO ISOOLEFINS AND ALKANOLS OVER ACID CATALYSTS

BACKGROUND OF THE INVENTION

1. Field of the Invention

The present invention relates to a process for the cleavage of alkyl tert-alkyl ethers by reactive distillation in the presence of acid catalysts to give the corresponding olefins and alkanols.

2. Background of the Invention

The cleavage of ethers, in particular alkyl tert-alkyl ethers, into alkanols and olefins, is a known reaction and can be used for the preparation of pure olefins. Thus, for example, isobutene is produced in technical-grade purity by dehydrogenation of $C_4$ mixtures. These $C_4$ mixtures comprise, apart from traces of $C_3$ and $C_5$ compounds, isobutene, 1-butene and 2-butene. Separation of this mixture by simple distillation to isolate pure isobutene is uneconomical because of the very small boiling point difference or separation factor for 1-butene and isobutene.

Pure isobutene is therefore usually prepared by cleavage of methyl tert-butyl ether (MTBE) back into isobutene and methanol.

The acid-catalyzed cleavage of ethers such as MTBE to prepare pure olefins such as isobutene is a process known per se. A distinction is made here between two different process variants. First, the cleavage can be conducted in the liquid phase over acid ion exchange resins as described, for example, in DE 3 509 292 A1 or DE 3 610 704 A1 or over acidic aluminum oxides as disclosed, for example, in DD 240 739 A1. In the latter case, the reaction conditions (167° C. and 1 bar or 297° C. and 10 bar) are selected so that the MTBE cleavage occurs in the gas/liquid region or in the pure gas phase.

Secondly, the cleavage reaction can be conducted in the gas/liquid phase in a type of combined reaction distillation column over acid catalysts, as disclosed in EP 0 302 336 A1 or DE 43 22 712. EP 0 302 336 A1 describes the elimination of methanol from MTBE over an acid ion exchange resin which is positioned in the bottom of the column. The cleavage of the ether here takes place in the bottom of the column, i.e. the catalyst is continually surrounded by a mixture of ether, olefin and alcohol. This is a disadvantage for the preparation of isobutene, since, first, it does not ensure that the isobutene which oligomerizes readily under acid conditions is removed quickly and, second, the acid centers of the catalyst are occupied by methanol. A different route is taken in DE 43 22 712. In this document, the tertiary ether is fed into a reaction distillation column above the reaction zone, and the rectification section of the column serves to purify the isobutene, while in the stripping section of the column, methanol is separated from the MTBE/methanol azeotrope. The azeotrope goes back into the reaction zone. Sulfated titanium dioxide extrudate is used as the acid catalyst.

In both procedures, catalyst poisons present in the feed, for example metal ions, can deactivate the Bronsted acid catalyst. In addition, the introduction of an MTBE/methanol mixture in this arrangement would decrease the rate of the MTBE cleavage reaction and thus reduce conversion. Methanol inhibits the actual cleavage reaction because it occupies the acid centers of the catalyst.

In the case of cleavage processes which are conducted in the pure liquid phase, it has to be noted that high MTBE conversions cannot be achieved in principle. This is because the cleavage reaction is a typical equilibrium reaction. Thus, for example, a liquid phase reaction at equilibrium at 100° C. and the corresponding total pressure has the following composition:

mol. fraction of isobutene=~15 mol. %
mol. fraction of MTBE=~70 mol. %
mol. fraction of methanol=~15 mol. %

Another problem of this process is the isobutene which is dissolved in the homogeneous liquid phase, which can undergo subsequent reactions. The most important reactions of this type are acid-catalyzed dimerization and oligomerization. For this reason, undesired $C_8$ and $C_{12}$ components are also found in addition to the desired isobutene product. The undesired $C_8$ molecules are 2,4,4,-trimethyl-1-pentene and 2,4,4,-trimethyl-2-pentene. Furthermore, because of the sometimes high reaction temperature, a subsequent reaction in which two methanol molecules react to form water and dimethyl ether. Since this reaction results in a considerable loss of methanol, fresh methanol has to be fed into the reaction, especially if the cleavage is integrated in a circuit with an MTBE synthesis.

In the process variant in which the cleavage reaction is conducted in the pure gas phase, the problems of dimerization or oligomerization of the isobutene formed to undesirable downstream products likewise occur. Dilution of the gaseous starting material stream with inert gas can reduce these reactions, but not eliminate them entirely. Dilution of the starting material stream at the same time reduces the efficiency of the production plant.

The reactions conducted in the gas phase or at high temperatures in the processes described have the disadvantage that high-boiling cracking products are formed during the cleavage process and deposit on the catalyst, thus deactivating it. Deactivated catalysts and/or high temperatures favor the formation of by-products and reduce the selectivity of the reaction. Particularly, the isobutenes obtained by ether cleavage tend to undergo undesirable thermal polymerization. If the cleavage reaction is conducted at lower temperatures, low conversions frequently result.

SUMMARY OF THE INVENTION

Accordingly, one object of the present invention is to provide a process for the cleavage of alkyl tert-alkyl ethers which achieves a high ether conversion together with low downstream product formation and low catalyst deactivation.

Briefly, this object and other objects of the present invention as hereinafter will become more readily apparent can be attained by a process for the cleavage of alkyl tert-alkyl ethers into the corresponding isoolefins and alkanols, comprising:

acid-catalyzed reactive distilling an alkyl tert-alkyl ether fed into the reaction zone of a reactive distillation apparatus as an azeotrope of the alkyl tert-alkyl ether and the corresponding alkanol, wherein the reactive distillation apparatus is configured from bottom to top as a bottom zone, at least one distillation zone and a reaction zone.

In another aspect of the invention, the alkyl tert-alkyl ether is fed into the reactive distillation apparatus below the reaction zone.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 1–6 show different embodiments of the reactive distillation apparatus employed in the acid-catalyzed reactive distilling of an alkyl tert-alkyl ether in the invention.

DETAILED DESCRIPTION OF THE PREFERRED EMBODIMENTS

It has surprisingly been found that the acid-catalyzed cleavage of alkyl tert-alkyl ethers into the corresponding olefins and alkanols can be conducted at high conversions and with low by-product formation when using the azeotrope of the ether and the corresponding alkanol to provide the high boiling ether in the reaction zone.

The present invention provides a process for the cleavage of alkyl tert-alkyl ethers into the corresponding isoolefins and alkanols by acid-catalyzed reactive distillation, wherein the reactive distillation apparatus has, in an upward direction, a bottom zone, at least one distillation zone and a reaction zone and, if desired, a further distillation zone and the alkyl tert-alkyl ether is fed into the reaction zone via an azeotrope of the alkyl tert-alkyl ether and the corresponding alkanol.

The particular advantages of the process of the invention are that the endothermic equilibrium reaction:

alkyl tert-alkyl ether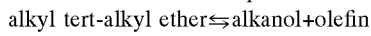alkanol+olefin occurring by ether cleavage in a reactive distillation apparatus is favorably influenced by removal of the olefin by distillation. Furthermore, the olefin concentration in the liquid phase is so low that the formation of undesired downstream products by dimerization:

2 olefin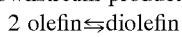diolefin or oligomerization is reduced compared to the pure liquid-phase process.

As catalyst in the process of the invention, it is possible to use an acid ion exchange resin or any other inorganic or organic acid catalyst. The acid catalyst can be located in conventional distillation/reaction packing made of woven metal mesh.

In the process of the invention, it is possible to cleave all alkyl tert-alkyl ethers which form a minimum azeotrope with the corresponding alkanol and can be cleaved in the presence of acid catalysts. The starting material for the process of the invention can therefore be a pure alkyl tert-alkyl ether or a mixture of the alkyl tert-alkyl ether with the corresponding alkanol and/or the isoolefin.

When using the pure ether, addition of the alkanol which is produced by the cleavage reaction is advisable. Although it is in principle possible to add other alkanols, the subsequent work-up of the alkanols is made more difficult. If separation is not necessary, i.e. the isoolefin is the actual product desired, it can be useful for the purpose of forming the azeotrope to add an alkanol other than that produced in the cleavage.

The cleavage of the alkyl tert-alkyl ethers of the invention leads to the corresponding olefins, i.e. generally to the branched olefins from the part of the ether molecule which bears the tertiary alkyl group. The tertiary alkyl part of these ethers from which the corresponding isoolefin subsequently results can contain from 3 to 10 carbon atoms.

The second cleavage product obtained is the corresponding alkanol. The alkyl part of the ether from which the corresponding alkanol subsequently results can be branched or unbranched and contains from 1 to 10 carbon atoms.

In the process of the invention, n-alkyl tert-alkyl ethers can be cleaved into n-alkanols and isoolefins, sec-alkyl tert-alkyl ethers can be cleaved into secondary alkanols and isoolefins, and tert-alkyl tert-alkyl ethers can be cleaved into tertiary alkanols and isoolefins. Examples of such compounds are:

| Alkyl tert-alkyl ether | Olefin | Alkanol |
|---|---|---|
| Methyl tert-butyl ether(MTBE) | Isobutene | Methanol |
| Ethyl tert-butyl ether (ETBE) | Isobutene | Ethanol |
| tert-Amyl methyl ether(TAME) | Isopentene | Methanol |
| tert-Amyl ethyl ether (TAEE) | Isopentene | Ethanol |
| tert-Butyl isopropyl ether (TBIPE) | Isobutene | Isopropanol |
| tert-Butyl sec-butyl ether (TBSBE) | Isobutene | 2-Butanol |
| tert-Butyl tert-butyl ether (TBTBE) | Isobutene | Isobutanol |

The alkyl tert-alkyl ether to be cleaved is fed into the reaction zone of the reaction distillation apparatus via an azeotrope of the ether and the corresponding alkanol.

A series of process variants can be used, and these are shown by way of example in FIGS. 1–6. In the Figures, E is the feed or introduction of the starting material, O is the olefin outlet, A is the alkanol outlet, R is the reaction zone, D, D1, D2, D3 indicate distillation zones, L is the emptying zone, whose presence is optional, and S is the bottom zone. The bottom zone is heated externally or internally, and the olefin outlet is provided with a condenser (not shown).

The azeotrope can be prepared by feeding the ether, i.e. the starting material, into the reactive distillation apparatus below the reaction zone, preferably between the reaction zone and the bottom zone, e.g. FIGS. 1 and 2. As the starting material, it is possible to use ether/alkanol mixtures of any composition. An appropriate MTBE/methanol mixture is frequently produced by MTBE production plants.

After the ether/alkanol azeotrope has been cleaved in the reaction zone, the corresponding olefin is removed from the top of the apparatus as olefin/alkanol azeotrope, while the major part of the alkanol runs to the bottom.

The alkanol/isoolefin azeotrope removed at the top may contain a small proportion of the ether.

In another embodiment of the process, the reactive distillation apparatus has a plurality of distillation zones, with one distillation zone being located above, i.e. downstream in the direction of gas flow, the reaction zone, e.g. FIGS. 5 and 6.

In another variant of the invention, it is possible for the alkyl tert-alkyl ether to be fed into the reactive distillation apparatus between distillation and reaction zones, e.g. FIG. 1. In FIG. 3, the starting material is fed in between two distillation zones. Furthermore, the ether can be fed into the apparatus in a distillation zone as shown in FIG. 4.

Surprisingly and advantageously, location of the catalyst packing or the reaction zone above the inlet for the starting material prevents catalyst poisons such as metal ions from reaching the reaction zone, so that deactivation of the catalyst is at least reduced. Furthermore, fractionation of an alkyl tert-alkyl ether/alkanol mixture to the azeotropic point is possible in the rectification section, so that alkyl tert-alkyl ether/alkanol mixtures of any composition can be processed. This ensures that an ether-containing liquid phase always reaches the reaction zone, so that the cleavage reaction does not stop.

Suitable column pressures for operation of the reactive distillation apparatus are in the range from 1 to not more than 15 bar, preferably not more than 10 bar. For the cleavage of MTBE, a column pressure of 3–7 bar has been found to be useful. If the catalyst used is, for example, a cation exchange resin, considerable elimination of sulfonic acid groups from the resin surface has to be expected at above 125° C., so that deactivation of the catalyst gradually takes place. In this case, a reaction temperature ranging from 80 to 120° C., preferably 105 to 115° C. is advisable.

The operating temperature which is optimal for the catalyst can be set via the column pressure.

Other catalysts which can be used in the process of the invention include, for example, acid-activated bentonites and/or aluminas, zeolites, sulfonated zirconium oxides and montmorillonites. These catalysts can be employed at higher temperatures, i.e., up to 200° C.

Location of the catalyst packing above the feed point prevents poisoning of the catalyst by metal ions which may be present in the feed stream. It is also possible to use ether/alkanol mixtures of any composition, since distillative fractionation of the mixture as far as the azeotrope can occur between the feed point and the reaction packing. This also enables the reaction temperature within the reaction zone to be controlled via the vaporization equilibrium, so that damage to the catalyst can be prevented. In this respect, processes which operate with the catalyst located in the bottom section have a considerable disadvantage because of possible overheating in the bottom section, so that damage to the catalyst can occur.

Having now generally described this invention, a further understanding can be obtained by reference to certain specific examples which are provided herein for purposes of illustration only and are not intended to be limiting unless otherwise specified.

The following example of the cleavage of MTBE into methanol and isobutene is intended to illustrate the present invention. The cleavage reaction of ethers such as ETBE, TAME, TAEE, TBIPE, TBSBE or TBTBE is conducted analogously.

The cleavage of MTBE is conducted in a pressure column which is equipped with distillation packing and reaction-distillation packing. The column, which is operated adiabatically, has the following dimensions and packing locations:

Internal diameter=80 mm
location of the packing elements:
-2nd–6th tray: distillation packing
-7th–13th tray: reaction packing
-14th–30th tray: distillation packing The starting material, consisting of 99% by weight of MTBE and 1% by weight of methanol, is subcooled to a temperature of 68° C. and fed at this temperature to the 20th tray at a rate of 2 kg/h. The subcooling of the starting material mixture is necessary for purely engineering reasons and has no influence on the reaction.

The column pressure is set at 6.5 bar. At the top of the column, the condenser is operated at about 52–53° C., so that the vapor stream can be completely condensed. Part of the condensed stream is discharged from the column while another part is returned to the column as runback. The reflux ratio is 9.

The temperature in the reaction zone under these boundary conditions ranges from 95 to 110° C. and should therefore lead to no damage to the styrene-divinylbenzene-based cation exchange resin installed in the reaction packing. The temperature at the bottom is about 120° C.

FIG. 6 schematically depicts the example described here; the compositions of the feed stream and of the distillate and bottoms streams are summarized in Table 1. The MTBE conversion in this example is over 99%. The starting material is fed into the apparatus via line F. The reactive distillation apparatus has two distillation zones D and D3, a treatable bottom zone B and a reaction zone R. Isobutene is removed as distillate stream O, and methanol is removed as bottoms stream A.

TABLE 1

Mass flows and main constituents of the streams are presented as rounded values.

| | kg/h | MTBE | Isobutene | Methanol |
|---|---|---|---|---|
| Feed stream | 2.00 | 99.0% by wt. | 0.0% by wt. | 1.0% by wt. |
| Distillate stream | 1.32 | 1.4% by wt. | 95.5% by wt. | 3.1% by wt. |
| Bottoms stream | 0.68 | 0.2% by wt. | 0.0% by wt. | 99.8% by wt. |

The disclosure of German priority Application No. 100 20 943.2 filed Apr. 28, 2000 is hereby incorporated by reference into the present application.

Obviously, numerous modifications and variations of the present invention are possible in light of the above teachings. It is therefore to be understood that within the scope of the appended claims, the invention may be practiced otherwise than as specifically described herein.

What is claimed as new and is intended to be secured by Letters Patents is:

1. A process for the cleavage of alkyl tert-alkyl ethers into the corresponding isoolefins and alkanols, comprising:
    acid-catalyzed reactive distilling an alkyl tert-alkyl ether fed into the reaction zone of a reactive distillation apparatus as an azeotrope of the alkyl tert-alkyl ether and the corresponding alkanol, wherein the reactive distillation apparatus is configured from bottom to top as a bottom zone, at least one distillation zone and a reaction zone
    wherein the azeotrope of the alkyl tert-alkyl ether is fed into a reactive distillation apparatus below the reaction zone of the reactive distillation apparatus.

2. The process as claimed in claim 1, wherein the alkyl tert-alkyl ether is fed into the reaction distillation apparatus between the reaction zone and the bottom zone.

3. The process as claimed in claim 1, wherein the alkyl tert-alkyl ether is fed into the reactive distillation apparatus between the distillation zone and the reaction zone.

4. The process as claimed in claim 1, wherein the reactive distillation apparatus has a plurality of distillation zones, with one distillation zone being located above the reaction zone.

5. The process as claimed in claim 1, wherein the alkyl tert-alkyl ether is fed into the distillation zone of a reaction distillation apparatus.

6. The process as claimed in claim 1, wherein n-alkyl tert-alkyl ethers are cleaved into n-alkanols and isoolefins.

7. The process as claimed in one of claim 1, wherein sec-alkyl tert-alkyl ethers are cleaved into secondary alkanols and isoolefins.

8. The process as claimed in one of claim 1, wherein tert-alkyl tert-alkyl ethers are cleaved into tertiary alkanols and isoolefins.

9. The process as claimed in one of claim 1, wherein methyl tert-butyl ether is cleaved into isobutene and methanol.

10. The process as claimed in one of claim 1, wherein ethyl tert-butyl ether is cleaved into isobutene and ethanol.

11. The process as claimed in one of claim 1, wherein tert-amyl methyl ether is cleaved into isopentene and methanol.

12. The process as claimed in one of claim 1, wherein tert-amyl ethyl ether is cleaved into isopentene and ethanol.

13. The process as claimed in one of claim 1, wherein tert-butyl isopropyl ether is cleaved into isobutene and isopropanol.

14. The process as claimed in one of claim 1, wherein tert-butyl sec-butyl ether is cleaved into isobutene and 2-butanol.

15. The process as claimed in one of claim 1, wherein tert-butyl tert-butyl ether is cleaved into isobutene and isobutanol.

16. The process as claimed in one of claim 1, wherein the alkyl tert-alkyl ethers is ethyl tert-butyl ether, tert-amyl methyl ether, tert-amyl ethyl ether, tert-butyl isopropyl ether, tert-butyl sec-butyl ether, or tert-butyl tert-butyl ether is conducted analogously.

17. The process as claimed in one of claim 1, wherein the cleavage reaction temperature in the reaction zone in the column ranges from 80 to 120° C.

18. The process as claimed in claim 1, wherein the alkyl tert-alkyl ether consists of a mixture of the alkyl tert-alkyl ether, an isoolefin and/or an alkanol.

* * * * *